US00PP27334P2

(12) United States Plant Patent
Green, Jr.

(10) Patent No.: US PP27,334 P2
(45) Date of Patent: Nov. 1, 2016

(54) ***CAMELLIA* PLANT NAMED 'GREEN 02-019'**

(50) Latin Name: *Camellia sasanqua*
Varietal Denomination: Green 02-019

(71) Applicant: Robert M. Green, Jr., Fairhope, AL (US)

(72) Inventor: Robert M. Green, Jr., Fairhope, AL (US)

( * ) Notice: Subject to any disclaimer, the term of this patent is extended or adjusted under 35 U.S.C. 154(b) by 64 days.

(21) Appl. No.: 14/545,159

(22) Filed: Mar. 31, 2015

(51) Int. Cl.
*A01H 5/02* (2006.01)

(52) U.S. Cl.
USPC ..... Plt./244

(58) Field of Classification Search
USPC ..... Plt./244
See application file for complete search history.

*Primary Examiner* — Anne Grunberg
(74) *Attorney, Agent, or Firm* — Penny J. Aguirre

(57) ABSTRACT

A new cultivar of *Camellia sasanqua* named 'Green 02-019', that is characterized by its compact, dense, and and spreading to rounded plant habit, its dark green foliage, its medium sized, double flowers that are soft pink in color with a rose form, its floriferous bloom habit with heavy bud set, its vigorous growth habit, and its resistance to root rot (*Phytophora cinnamomi*) and dieback (*Glomerella cingulata*).

2 Drawing Sheets

Botanical classification: *Camellia sasanqua.*
Variety denomination: 'Green 02-019'.

BACKGROUND OF THE INVENTION

The present invention relates to a new and distinct cultivar of *Camellia* plant, botanically known as *Camellia sasanqua*, 'Green 02-019'. The new cultivar will be referred to hereafter by its cultivar name, 'Green 02-019'. 'Green 02-019' is a new perennial shrub grown for container and landscape use.

'Green 02-019' was derived from an ongoing breeding program conducted by the Inventor in Fairhope, Ala. The objectives of the breeding program are to develop new cultivars of *Camellia sasanqua* with compact plant habits, vigorous growth habits, improved disease resistance, and extended bloom periods. 'Green 02-019' originated as a seedling that arose from seed planted from crosses between unnamed plants and unpatented plants of *Camellia sasanqua* from the Inventor's breeding program in Fall of 2000 in Fairhope, Ala. The exact parentage is therefore unknown as seeds where pooled from seveal crosses. The new *Camellia* was selected as a single unique plant in Fall of 2005.

Asexual propagation of the new cultivar was first accomplished by stem cuttings by the Inventor in Fall of 2005 in Fairhope, Ala. Asexual propagation by stem cuttings has determined that the characteristics of this cultivar are stable and are reproduced true to type in successive generations.

SUMMARY OF THE INVENTION

The following traits have been repeatedly observed and represent the characteristics of the new *Camellia*. These attributes in combination distinguish 'Green 02-019' as a new and distinct cultivar of *Camellia.*

1. 'Green 02-019' exhibits a compact, dense, and spreading to rounded plant habit.
2. 'Green 02-019' exhibits dark green foliage.

3. 'Green 02-019' exhibits medium sized, double flowers with a rose form that are soft pink in color.
4. 'Green 02-019' exhibits a floriferous bloom habit with heavy bud set.
5. 'Green 02-019' exhibits a vigorous growth habit.
6. 'Green 02-019' exhibits resistance to root rot (*Phytophora cinnamomi*) and dieback (*Glomerella cingulata*).

'Green 02-019' can also be compared to the cultivars 'Shi-Shi-Gashira' (not patented), 'Showa-No-Sakae' (not patented) and 'Stephanie Golden' (not patented). 'Shi-Shi-Gashira' is similar to 'Green 02-019' in having a dense plant habit, good disease resistance, and in having a long blooming period. 'Shi-Shi-Gashira' differs from 'Green 02-019' in having flowers that are smaller and deeper rose in color with less petals, and in having a slightly more open growth habit. 'Showa-No-Sakae' is similar to 'Green 02-019' in having flowers that are similar in color and in having a similar growth habit when young. 'Showa-No-Sakae' differs from 'Green 02-019' in having a less dense plant habit, much less disease resitance and in having smaller flowers that are lighter pink in color and peony-formed. 'Stephanie Golden' is similar to 'Green 02-019' in having good disease restance, a dense plant habit, good vigor and dark green foliage. 'Stephanie Golden' differs from 'Green 02-019' in having slightly smaller flowers that are brighter pink in color, more double and peony-formed, and in having a more upright plant habit.

BRIEF DESCRIPTION OF THE DRAWINGS

The accompanying colored photographs illustrate the overall appearance and distinct characteristics of the new *Camellia*. The photographs were taken of a five year-old plant of 'Green 02-019' as grown outdoors in a trial garden in Fairhope, Ala.

The photograph in FIG. 1 provides a close-up view of the flowers of 'Green 02-019'.

Figure 1:
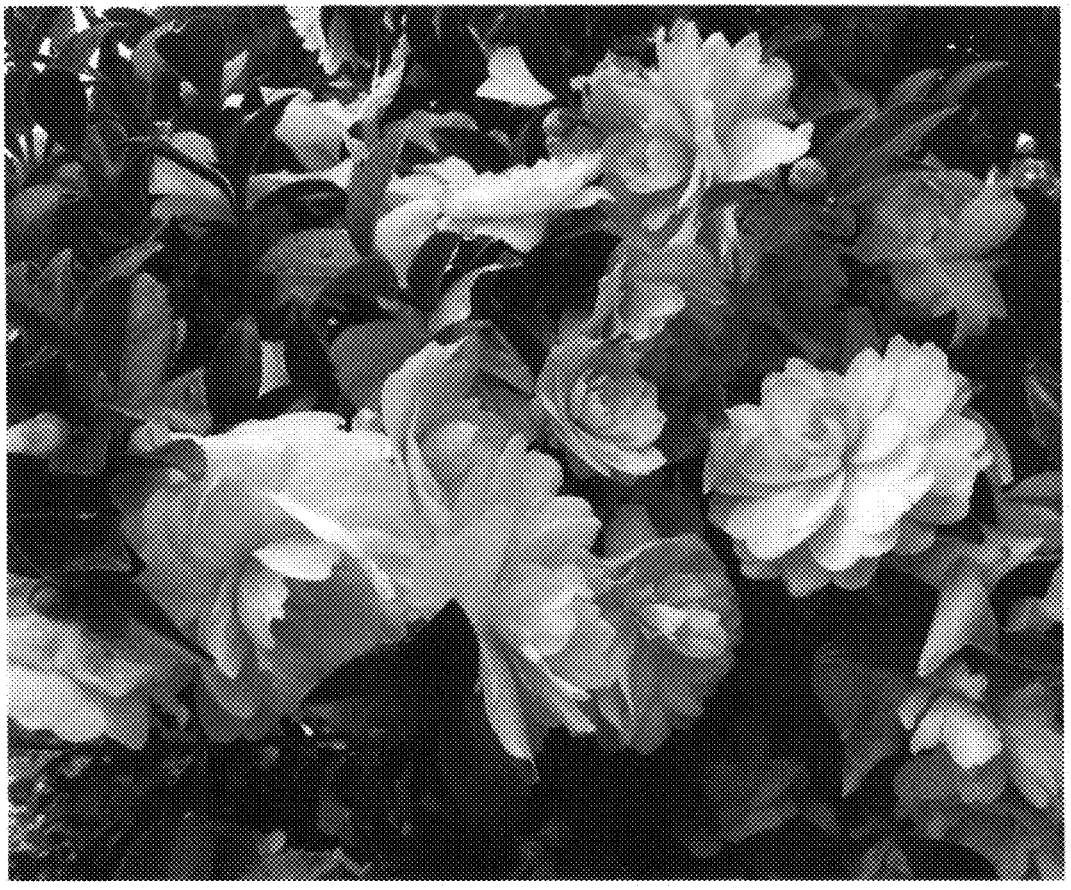
Figure 2:
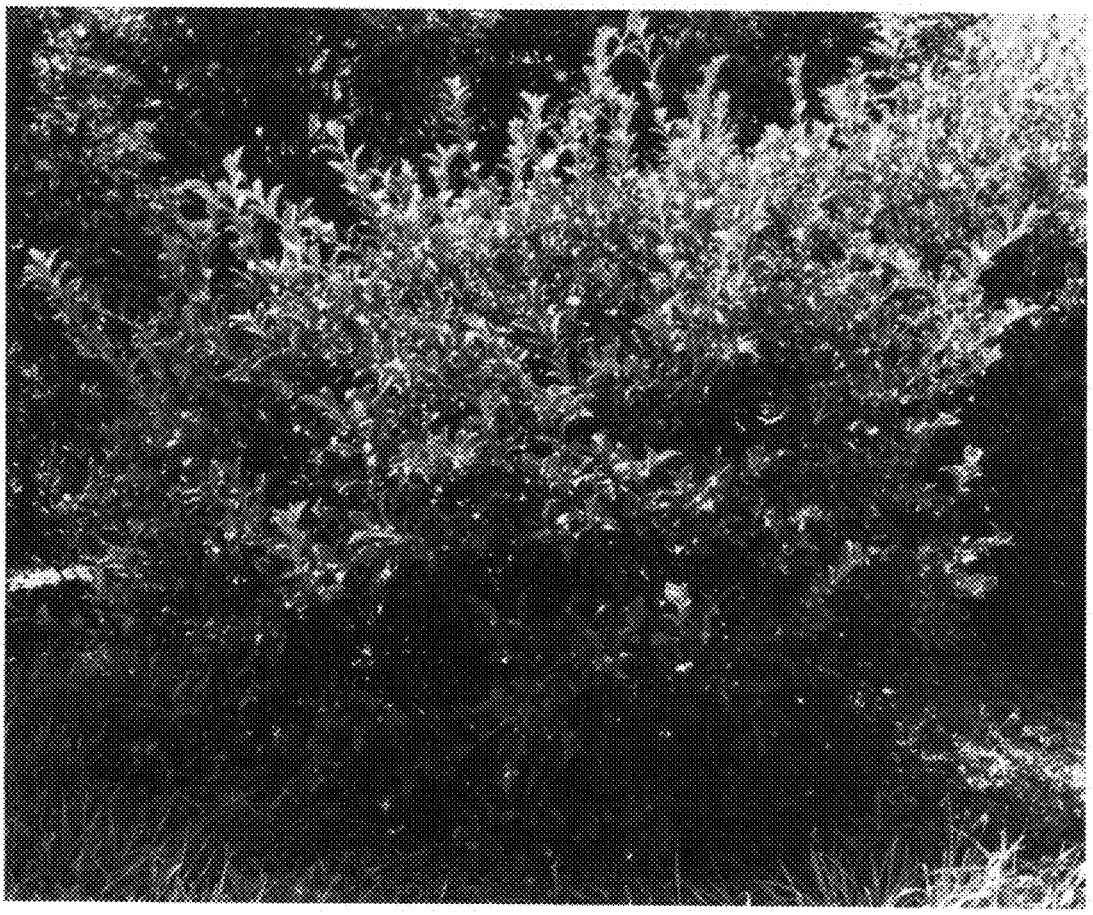

The photograph in FIG. 2 provides a side view of the plant habit of 'Green 02-019'.

The colors in the photographs are as close as possible with digital photography techniques available, the color values cited in the detailed botanical description accurately describe the colors of the new *Camellia*.

DETAILED BOTANICAL DESCRIPTION

The following is a detailed description of three year-old plants of the new cultivar as grown ourtdoors in three-gallon containers in Fairhope, Ala. Plants were grown under 30% shade cloth with average day temperatures between 10 to 24° C. (50 to 75° F.) and average night temperatures between −1 to 10° C. (30 to 50° F.). The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit*.—Six to eight weeks beginning in mid to late fall in Fairhope, Ala.

*Plant type*.—Evergreen shrub.

*Plant habit*.—Compact, dense, and spreading to rounded in shape.

*Height and spread*.—An average of 1.3 m in height and spread when mature in the landscape.

*Hardiness*.—At least hardy in U.S.D.A. Zones 7 to 9.

*Diseases and pests*.—Has shown resistance to root rot (*Phytophora cinnamomi*) and dieback (*Glomerella cingulata*).

*Propagation*.—Stem cuttings.

*Time required for root initiation*.—An average of 40 days.

*Time required for root development*.—An average of 6 months to fully develop in a 3 inch container.

*Growth rate*.—Vigorous.

Branch description:

*Stem shape*.—Round.

*Stem strength*.—Strong.

*Stem color*.—Young; 165A, mature bark; 200C suffused with 165A at the base with 166B towards the middle.

*Stem size*.—Main laterals; average of 70 cm in length and 3 mm in width, secondary laterals; an average of 35 cm in length and 2 mm in width.

*Stem surface*.—Young; bark-like, slightly glossy and sparsely covered with soft pubescent hairs an average of 0.5 to 1 mm in length, and 165A in color, mature; bark- like, slightly rough to touch.

*Branching*.—Densely branched with an average of 15 main lateral branches and 12 to 18 secondary lateral branches per main laterals.

Foliage description:

*Leaf shape*.—Elliptic to nearly ovate to narrowly elliptic.

*Leaf division*.—Simple.

*Leaf base*.—Cuneate.

*Leaf apex*.—Bluntly acuminate to acute.

*Leaf fragrance*.—None.

*Leaf margins*.—Serrate.

*Leaf arrangement*.—Alternate.

*Leaf attachment*.—Petiolate.

*Leaf substance*.—Young leaves; thick and rubbery, mature leaves; thick.

*Leaf surface*.—Upper surface; smooth, glabrous, and very glossy, lower surface; sparsely pubescent and satiny.

*Leaf size*.—An average of 4.5 cm in length and 2.5 cm in width.

*Leaf quantity*.—An average of 13 per branch 20 cm in length.

*Leaf venation*.—Pinnate, inconspicuous except mid rib, midrib on upper surface 146B in color and covered with short hairs an average of 0.25 to 0.5 mm in length, midrib on lower surface 145A in color.

*Leaf color*.—Young and mature leaves upper surface; a blend of 139A and N137A, young and mature leaves lower surface; 146A.

*Petioles*.—Rounded and slightly flattened in shape, an average of 2 mm in width and 5 mm in length, sparsely pubescent, 144A in color.

*Stipules*.—None.

Inflorescence description:

*Inflorescence type*.—Single, rotate double flowers.

*Flower number*.—An average of 4 to 5 per lateral stem.

*Flower fragrance*.—Slightly fragrant, faintly rose-like.

*Flower longevity*.—About one week, self cleaning.

*Flower type*.—Solitary, rotate double.

*Flower aspect*.—Outward to slightly upright.

*Flower size*.—An average of 6 cm in diameter and 2 cm in depth.

*Peduncles*.—None, flowers are sessile to stem.

*Flower buds*.—Globose in shape, an average of 2 cm in length and width, color 144B with apex 70A.

*Sepals*.—An average of 6, ovate to rounded in shape and strongly cupped inward, imbricate, an average of 1.2 cm in length and 1 cm in width, rounded to emarginate apex, truncate base, entire margin, color; outer and inner surface 144B with base 145C and margins 70A, lightly suffused with 199B to 199D, upper surface midrib covered with silky hairs, inner surface glabrous and satiny.

*Petals*.—36 to 45, upper and lower surfaces; glabrous and dull, entire margins, cordate apex, broadly cuneate base, outer petals; cordate to oblong in shape, an average of 3.5 cm in length and 2.5 cm in width, inner petals; oblong in shape, an average of 1.5 cm in length to 1 cm in width, color: upper and lower surfaces when opening; 70C to 70D, upper and lower surfaces when fully open; 70B to 70D.

Reproductive organs:

*Pistil*.—Rudimentary, nonfunctional, 145D in color.

*Stamens*.—Few, sparse, and, mal-formed, about 3 mm in length and 155A in color, pollen; none detected

*Fruit and seed*.—None have been observed, essetially sterile.

It is claimed:

1. A new and distinct cultivar of *Camellia* plant named 'Green 02-019' as herein illustrated and described.

* * * * *